United States Patent [19]

Civerchia

[11] Patent Number: 5,114,627
[45] Date of Patent: May 19, 1992

[54] METHOD FOR PRODUCING A COLLAGEN HYDROGEL

[75] Inventor: Linda Civerchia, Ft. Lauderdale, Fla.

[73] Assignee: CBS Lens, Santa Maria, Calif.; a California general partnership

[21] Appl. No.: 624,346

[22] Filed: Dec. 6, 1990

Related U.S. Application Data

[60] Division of Ser. No. 402,986, Sep. 1, 1989, Pat. No. 4,983,181, which is a continuation of Ser. No. 920,031, Oct. 16, 1986, abandoned.

[51] Int. Cl.⁵ .................. B29D 11/00; C08H 1/00
[52] U.S. Cl. .................. 264/1.1; 264/1.4; 264/2.6; 264/22; 264/28; 264/41; 264/233; 264/330; 522/87; 523/105; 523/106; 523/114; 523/449
[58] Field of Search .................. 264/1.1, 2.6, 2.7, 1.4, 264/22, 28, 41, 233, 330; 351/160 H; 522/87; 523/105, 106, 114, 449

[56] References Cited

U.S. PATENT DOCUMENTS

| | | | |
|---|---|---|---|
| 4,388,428 | 6/1983 | Kuzma et al. | 351/160 H |
| 4,452,776 | 6/1984 | Reforjo | 264/2.7 |
| 4,452,925 | 6/1984 | Kuzma et al. | 351/160 H |

Primary Examiner—James Lowe
Attorney, Agent, or Firm—Daniel J. Meaney, Jr.

[57] ABSTRACT

A method of making a collagen-hydrogel is shown. The method comprises the steps of forming a radical free polymer of a hydrophilic monomer; mixing the hydrophilic monomer with a stock solution of collagen in the presence of a weak solution of ammonium persulfate and sodium metabisuleate forming a clear viscous monomer solution; and heating said viscous monomer solution in the presence of a crosslinking agent to polymerize the same into a three dimensional polymeric meshwork having collagen from the stock solution of collagen interdispersed within the three dimensional polymeric meshwork.

27 Claims, 3 Drawing Sheets

METHOD FOR PRODUCING A COLLAGEN HYDROGEL

This is a division of application Ser. No. 07/402,986 filed Sep. 1, 1989, which issued as U.S. Pat. No. 4,983,181 on Jan. 8, 1991, which was a continuation of application Ser. No. 06/920,031 filed Oct. 16, 1986, now abandoned.

BACKGROUND OF THE INVENTION

1. Field of the Invention

This invention relates to a collagen-hydrogel material which contains a collagen-hydrogel for promoting epithelial cell growth and which is adapted to be used to fabricate artificial lens or contact lens which promotes healing of corneal epithelium during implantation and more particularly to a collagen-hydrogel biomedical material that is formed of a polymerized hydrophilic monomer which is gelled and crosslinked to form a polymeric meshwork in the presence of and anchoring macromolecules formed of a constituent of ground tissue capable of promoting and sustaining epithelial cell growth and wherein an artificial lens, formed of the collagen-hydrogel for promoting epithelial cell growth and positioned over the pupillary zone of the eye contiguous Bowman's membrane having a selected portion of corneal epithelium removed therefrom, promotes epithelial cell growth enabling corneal epithelium to attach to and cover the artificial lens to implant the same in the eye between Bowmann's membrane and a new layer of epithelial cells forming corneal epithelium.

2. Description of the Prior Art

Before beginning a description of the prior art, it would be helpful, in understanding the teachings of this invention, to define certain of the key terms that are used in the teachings of this invention.

Collagen, in its broadest sense, is a natural protein which serves as the ground substance or adhesive substance between cells in living tissue. It is well known in the art that collagen, as a substrate material, is capable of promoting cell adhesion and growth. Other proteins are also known to be capable of supporting cell growth of at least certain cell lines. In the present invention, the preferred source of collagen, as a natural protein, is derived from animal sources.

It is also known that other macromolecules, that is a molecule formed of a constituent of a ground substance of tissue, can support cell growth. Typical of such macromolecules, in addition to collagen, are mucopolysaccharides or fibronectin, which constituents of ground substances of tissue are capable of promoting cell growth.

One class of synthetic materials which have found wide application as biomaterials is the class known as hydrogels. The term "hydrogel" refers to a broad class of polymeric materials which are swollen extensively in water, but which do not dissolve in water. Generally, hydrogels are formed by polymerizing a hydrophilic monomer in an aqueous solution under conditions where the polymer becomes crosslinked so that a three dimensional polymer network is formed which is sufficient to gel the solution.

Hydrogels are described in more detail in Hoffman, D. S., "Polymers in Medicine and Surgery," Plenum Press, New York, pp 33-44 (1974).

Hydrogels have many desirable properties for biomedical applications. For example, they can be made nontoxic and compatible with tissue. In addition, they are usually highly permeable to water, ions and small molecules. As is noted herein below, despite these favorable qualities, hydrogels have been found, in general, to be unsuitable as substrates for cell attachment and growth.

With the benefit of the above described descriptions and definitions, the known prior art will now be addressed.

It is known in the art to utilize a procedure known as epikeratophakia for the correction of aphakia and high myopia in a human eye (hereinafter referred to as the "Epikeratophakia Procedure"). In the Epikeratophakia Procedure, human corneal tissue is used and the corneal tissue is mechanically machined or polished to a specific lens power to form a corneal tissue lens. The corneal tissue lens is then sutured to the anterior surface of the cornea in the pupillary zone of the eye in order to change the refractive power of the eye. The specific procedure used for suturing the machined or polished corneal tissue lens to the eye requires that a portion of corneal epithelium be removed to expose a portion of Bowman's membrane and corneal tissue lens then be placed directly upon Bowman's membrane. During the healing process, corneal tissue lens is covered by epithelial cells which form the cornea epithelium implanting corneal tissue lens between Bowman's membrane and corneal epithelium. This procedure depends on the availability of human cornea tissue.

It is also known in the art to use frozen human corneal tissue, which is ground to a lenticular power, to form a corneal tissue lens and to suture the same to corneal stroma of a human eye to change the refractive power of the eye. This procedure is known as the "keratomileusis" and is described in a published article captioned "Keratophakia and Keratomileusis—Clinical Results" which appeared in August 1981, Volume 88, No. 8, at pages 709-715 of *American Academy of Opthalmology* by Swinger, Casmir and Barraquer, Jose' (the "Swinger/Barraquer Publication").

It is also known in the art to use collagen-hydroxyethylmethacrylate hydrogels as substrates for promoting cell growth in tissue culture. The material used for the hydrogel is known as collagen-hydroxeythylmethacrylic, and referred to as a HEMA hydrogel, which was prepared in the presence of an aqueous solution of native collagen. The resulting transparent hydrogel containing collagen was evaluated as substrata for growth of various cell lines in tissue culture. The preparation and use of collagen-hydroxyethylmethacrylate hydrogels for promoting cell growth in tissue culture is described in a article entitled USE A COLLAGEN-HYDROXYETHYLMETHACRYLATE HYDROGEL FOR CELL GROWTH which appeared in Volume 77, Number 4, April 1980 at pages 2064-2068 of the Proceedings of the National Academy of Science, United States of America, wherein the authors were Linda Civerchia-Perez (the inventor herein), Barbara Faris, Gary La Pointe, John Beldekas, Howard Leibowitz and Carl Franzblau (the "Civerchia Publication"). The Civerchia Publication disclosed that the collagen-hydroxyethylmethacrylate hydrogels for promoting cell growth in tissue culture were prepared by polymerizing monomeric hydroxyethylmethacylate in the presence of various concentrations of soluble native collagen. The resulting transparent hydrogels were used as substrate for growth of IMR-90 human embryonic lung fibroblasts. It was determined from these experiments that the growth of IMR 90 human embryonic lung fibroblasts was dose dependent upon the amount of collagen contained within the hydrogel. The resulting cell growth become intimately attached to the hydrogel substrate, and could not be removed. It was also noted during the experiments leading to the Civerchia Publication that hydrogels containing albumin, gelatin (denatured collagen) or collagenase-treated collagen do not support cell growth. The results of this publication provided a foundation for a relatively easy procedure for experimentally probing mechanisms of cell adhesion and cell differention.

The use of hydrogels for the correction of refractive error is well known in the art, and such hydrogels are used as the base material for fabricating soft contact lens. Soft contact lens are adapted to be inserted into and removed from the eye. When soft contact lens are placed in the eye of a user, the function thereof is to correct myopia, hyperopia, astigmatism, and aphakia. Typically such contact lens are formed of a hydrogel selected from the hydrophilic class of polymers, and the hydrogel is molded or lathed to a specific lens power. The soft contact lens, when placed over the pupillary zone of the eye of a user, rests upon a tear film and corneal epithelium and function to change the refractive power of the eye.

It is also known in the art to experimentally implant high water content, intracorneal implants fabricated from a Vistamarc hydrogel in the eye of rhesus monkeys and to develop keratometric data therefrom. Typical of publications describing this procedure are (i) an article captioned HYDROGEL KERATOPHAKIA: A FREEHAND POCKET DISSECTION IN THE MONKEY MODEL which appeared in the 1986 Volume 70 issue, at pages 187-191 of the British Journal of Ophthalmology by Bernard E. McCarey et al (the "McCarey Publication"), and (ii) an article captioned HYDROGEL KERATOPHAKIA: A MICROKERATOME DISSECTION IN THE MONKEY MODEL which appeared in the 1986 Volume 70 issue, at pages 192-198 of the British Journal of Ophthalmology by W. Houdijn Beekuis et al (the "Beekuis Publication"). These publications disclose that hydrogels can be implanted into the cornea of a monkey and that the hydrogel materials are compatible with the cornea tissue of a monkey.

U.S. Pat. No. 4,126,904 to Dennis D. Shepard, M. D. discloses artificial lenses, which are hard contact lenses, which are adapted to be placed in the eye of a user. In addition, U.S. Pat. No. 4,126,904 discloses a method of locating the same on the cornea of the eye. The disclosed artificial lens has an optical portion, which preferably is circular in shape and dimensioned to overlie the pupillary zone of an eye, and a non-optical portion, termed the "haptic" portion, which is used as a means for permanently affixing the lens to the eye. As taught by U.S. Pat. No. 4,126,904, the artificial lens can be affixed to the anterior surface of the cornea by suturing, stapling or like attachment means for securing the lens to adjacent structure of the eyeball so that the lens will move with the eyeball.

SUMMARY OF THE INVENTION

None of the prior art discloses, teaches or suggests a collagen-hydrogel which is capable of promoting epithelial cell growth when fabricated into an artificial lens which is positioned over the pupillary zone of the eye contiguous with Bowman's membrane to promote and support epithelial cell growth enabling corneal epithelium to become attached to and implant the artificial lens between Bowman's membrane and corneal epithelium.

This invention relates to the use of a transparent collagen-hydrogel, as a biomedical material, which is capable of being molded to a given lenticular power as in the preparation of a contact lens, to produce an artificial lens having a collagen-hydrogel for promoting epithelial cell growth. Such an artificial lens is adapted to be sutured, glued, or held in place with bandage or therapeutic contact lens until the epithelium growth occurs directly to the anterior surface of the cornea directly on Bowman's membrane and functions to correct refractive errors of the eye. The collagen-hydrogel, referred to sometimes herein as a "collagen-hydrogel for promoting epithelial cell growth," will be covered by corneal epithelium during the healing process. The growth of the epithelial cells to form corneal epithelium on the anterior surface of the eye during the healing process is very similar to that experienced in the Epikeratophakia Procedure.

In the present invention, a hydrogel polymer is disclosed that is formed by the free radical polymerization of a hydrophilic monomer solution gelled and crosslinked to form a three dimensional polymeric meshwork anchoring macromolecules. The macromolecules comprise a constituent of a ground substance of tissue, such as a native collagen, interspersed within the polymeric meshwork forming a collagen-hydrogel for promoting epithelial cell growth. An optical lens for the eye fabricated from the collagen-hydrogel, when attached to Bowman's membrane of the cornea of an eye, is capable of supporting and promoting epithelial cell growth enabling corneal epithelium to attach to and cover an artificial lens formed of the collagen-hydrogel for promoting epithelial cell growth during the healing process.

Also disclosed herein is an artificial lens, which preferably is a contact lens having a predetermined shape and power, which is fabricated from the collagen-hydrogel biomedical material and which is adapted to be affixed to Bowman's membrane of the cornea of an eye. When the artificial lens formed of the collagen-hydrogel for promoting epithelial cell growth is so affixed to the eye, it promotes and supports growth of epithelial cells across the surface thereof to produce corneal epithelium formed of several layers of epithelial cells. In the preferred embodiment, the contact lens comprises a lens body having anterior and posterior surface and formed of a collagen-hydrogel for promoting epithelial cell growth. The hydrogel comprises a hydrogel polymer formed by the free radical polymerization of a hydrophilic monomer solution gelled and crosslinked to form a three dimensional polymeric meshwork anchoring macromolecules. The macromolecules comprise a constituent of a ground substance of tissue interspersed within the polymeric meshwork forming a collagen-hydrogel for promoting epithelial cell growth. The collagen-hydrogel is capable of promoting and supporting growth of corneal epithelium formed of several layers of epithelial cells which implant the artificial lens between Bowman's membrane and corneal epithelium. The lens body is adapted to have the posterior surface thereof positioned, over the pupillary zone of the eye, and is affixed to Bowman's membrane in an area substantially equal to the shape of the lens body having corneal epithelium removed therefrom. When the lens body is so affixed, it is capable of supporting and promoting epithelial cell growth enabling corneal epithelium to attach to and cover the anterior surface of the lens body.

Also disclosed herein is a method of fabricating a collagen-hydrogel for promoting epithelial cell growth. The method comprises the steps of forming a radical free polymer of a hydrophilic monomer; mixing the hydrophilic monomer with a diluted solution of macromolecules comprising a constituent of ground substance of tissue in the presence of a weak solution of ammonium persulfate and sodium metabisulfate forming a clear viscous monomer solution; and heating the polymer mixture in the presence of a crosslinking agent to polymerize the same into a three dimensional polymeric meshwork having macromolecules comprising a constituent of ground substance of tissue interspersed within the three dimensional polymeric meshwork.

The hydrogel used in the prior art for lenses which are placed onto the cornea of the eye or implanted on the eye have serious disadvantages which are overcome by the teachings of this invention.

The Epikeratophakia Procedure and the procedure described in the Barraquer Publication require the use of human corneas as the source of corneal tissue. The corneal tissue must be processed into a predetermined shape and power to fabricate an implantable corneal tissue lens. The source of human corneal tissue is limited, and the cost thereof is controlled, thereby limiting the availability of the corneal tissue for the Epikeratophaki Procedure and the use of the Epikeratophakia Procedure itself as a readily available alternative.

None of the prior art which disclose the use of collagen-hydrogel for fabricating artificial lens disclose, teach, or suggest the use of a collagen-hydrogel which has been gelled and crosslinked to form a three dimensional polymeric meshwork anchoring macromolecules wherein the macromolecules comprise a constituent of a ground substance of tissue interspersed within the polymeric meshwork forming a collagen-hydrogel for promoting epithelial cell growth when the hydrogel is attached to Bowman's membrane of the cornea of an eye. As a result of collagen-hydrogel for promoting epithelial cell growth, corneal epithelium is capable of attaching to and covering the collagen-hydrogel.

The prior art Civerchia Publication discloses the experimental use of a collagen-hydroxyethylmethacrylate hydrogel as tissue growing substrate for promoting tissue cell growth of IMR-90 human embryonic fibroblasts, which are cells harvested from the lungs of a human fetus, as an experimental means to probe the mechanism of cell adhesion and cell differention. Thus, the teachings of the Civerchia Publication are limited to experimental tissue culture applications in that the Civerchia Publication did not recognize, teach, suggest, or disclose either the concept of or the use of a collagen-hydrogel for promoting epithelial cell growth as a basic material for fabrication of an artificial lens which, when implanted on, or into, the eye, would result in overcoming rejection of the artificial lens and the promotion of and support of the growth of epithelial cells to enable corneal epithelium to attach to and cover the anterior surface of the artificial lens with several layers of epithelial cells to form corneal epithelium resulting in the artificial lens being implanted between Bowman's membrane and corneal epithelium.

The McCarey Publication and Beekuis Publication disclose the implantation of artificial lens, using the freepocket dissection method and the Barraquer method, respectively, wherein the artificial lenses were fabricated from hydrogels with high water content. The results disclosed by both the McCarey Publication and Beekuis Publication were that the hydrogels were well tolerated within the corneal tissue. The Beekuis Publication disclosed that the implantation of hydrogels had interface problems along the edge; of implant, apparently from tissue buildup at the boundary layer between the lens/corneal epithelium interface. The Beekuis Publication noted that implants with abruptly cut edges versus a fine wedge tended to have more light scattering collagen at the implant margin. The collagen referred to is the native corneal collagen located within the corneal tissue of the monkey, and to native collagen. There is no collagen interspersed within the hydrogel molecular structure that was used to fabricate the artificial lens implanted within the monkeys as described in both the McCarey Publication and Beekuis Publication.

The artificial lens and method for implanting the same disclosed in U.S. Pat. No. 4,126,904 relates to so called "hard contact lens", and the lens are formed of standard plastics or known hard plastics, such as polymethylmetacrylate (PMMA), none of which contain a collagen-hydrogel for promoting epithelial cell growth. The concept of surgically positioning the artificial lens, over the pupillary zone of the eye is applicable to this invention, it being noted, however, that the artificial lens attached to the eye using the teachings of U.S. Pat. No. 4,126,904 results in the lens being affixed to the anterior surface of corneal epithelium.

Thus one advantage of the present invention is that the collagen-hydrogel material for promoting epithelial cell growth can be used as the base material for fabrication of artificial lens of a reproducable power and quality as is well known in the art for producing contact lens. The collagen-hydrogel artificial lens can be reproduced reliably in the laboratory and is not dependent upon the availability of human tissue as is the case in the production of a corneal tissue lens as described by the prior art.

Another advantage of the present invention is that the artificial lens fabricated from the collagen-hydrogel for promoting epithelial cell growth of the present invention and implanted on the eye results in the elimination of rejection of the artificial lens by the cornea and promotes and supports growth of epithelial cells during the healing process to actually implant the lens between Bowman's membrane and a new layer of corneal epithelium grown from the epithelial cells.

Another advantage of the present invention is that the artificial lens can be fabricated to any selected geometrical shape or diopter power from the collagen-hydrogel for promoting epithelial cell growth using any one of molding, lathing or freezing processes.

Another advantage of the present invention is that the collagen-hydrogel for promoting epithelial cell growth enables corneal epithelium to attach to and cover the anterior surface of an artificial lens implanted within the eye because of the growth of epithelial cells which produce a corneal epithelium having several layers of cell thickness resulting in the artificial lens being implanted between Bowman's membrane and corneal epithelium.

Another advantage of the present invention is that the implantation of the artificial lens requires only the removal of corneal epithelium from the surface of the cornea and the formation of a small "V" shaped slot and corneal wing which does not disturb the integrity of the cornea any more than a corneal abrasion or a superficial corneal laceration. The artificial lens is covered with epithelial cells during the healing process.

Another advantage of the present invention is that the necessity of maintaining a "tear layer" between the posterior surface of a soft contact lens and corneal epithelium is eliminated.

Another advantage of the present invention is that when the epithelial cells attach to and cover the anterior surface of an artificial lens fabricated from the collagen-hydrogel for promoting epithelial cell growth, if it ever becomes surgically necessary to remove and replace the artificial lens, such as for example in an accident damaging the eye, the collagen-hydrogel can be stripped from Bowman's Membrane and corneal epithelium can regrow over a defect, or a new collagen-hydrogel can be placed which will support regrowth of corneal epithelium. This is one of the basic advantages of the Epikeratophakia Procedure. That advantage is that a corneal overlay is less invasive to the eye than a corneal inlay.

Another advantage of the present invention is that the collagen-hydrogel for promoting epithelial cell growth disclosed herein is formed by the free radical polymerization of a hydrophilic monomer solution gelled and crosslinked to form a three dimensional polymeric meshwork anchoring macromolecules, comprising a constituent of a ground substance of tissue, which are interspersed within said polymeric meshwork forming a collagen-hydrogel for promoting epithelial cell growth.

Another advantage of the present invention is that the macromolecules may be a native collagen derived from animal sources and capable of promoting and supporting growth of epithelial cells.

Another advantage of the present invention is that the sources of native collagen can be harvested from tissues of human cornea, livestock cornea or calf's or livestock skins, all of which are widely available in an almost unlimited supply and at a reasonable cost.

Another advantage of the present invention is that the hydrogel can be formed from a hydrophilic monomer such as hydroxyethyle- methacrylate.

Another advantage is that hydrogel can be polymerized in the presence of a crosslinking agent to form a three dimensional polymeric meshwork having controlled spacings between the molecules thereof to anchor the macromolecules which have a known size and to insure that the macromolecules will be substantially uniformly interspersed within the polymeric meshwork of the polymerized hydrophilic monomer.

Another advantage of the present invention is that the step of forming the crosslinking of the hydrogel can be performed with a crosslinking agent which may be external, such as for example ultraviolet radiation, or a crosslinking agent added to the hydrogel clear viscous monomer solution, which crosslinking agent may be, for example, ethylene glycol dimethacrylate or methymethacrylate.

Another advantage of the present invention is that the artificial lens can be formed of the collagen-hydrogel for promoting epithelial cell growth of the present invention wherein the artificial lens has an optical portion configured for placement over the pupillary zone of the eye and on the central anterior surface of Bowman's membrane of the cornea having corneal epitheleum thereof removed. The optical portion of the artificial lens is dimensioned to substantially cover the total anterior surface of the pupillary zone of an eye.

Another advantage of the present invention is that a method of fabricating a collagen-hydrogel for promoting epithelial cell growth which, when positioned contiguous to Bowman's membrane and corneal epithelium of the cornea of an eye, promotes and supports epithelial cell growth to form a corneal epithelium is disclosed herein.

Another advantage of the present invention is that a method for locating on the cornea an artificial lens having a preselected geometric shape and power and including an optical portion having an outer edge, a posterior surface and an anterior surface is disclosed herein.

Another advantage of the present invention is that the method for locating on the cornea an artificial lens having a preselected geometric shape and power includes the steps of removing from Bowman's membrane over the pupillary zone of the eye a portion of corneal epithelium on an area slightly greater than the generalized shape of said artificial lens; forming on Bowman's membrane and corneal stroma a "v" shaped annular groove having a diameter substantially equal to the maximum geometrical dimensions of the artificial lens and defining therearound a peripheral and medial edge and having a preselected depth which is less than the thickness of the corneal stroma; dissecting the peripheral edge of said groove forming a wing of corneal tissue having a preselected length; separating the medial edge of the groove from the corneal groove; placing the posterior surface of said artificial lens on the anterior surface of the cornea and positioning the outer edge of said artificial lens under the corneal wing, and affixing the artificial lens to the cornea over the pupilary zone of the eye to maintain the same on the cornea with the posterior surface in contact with Bowman's membrane and the corneal wing overlying the edge of the artificial lens enabling corneal epithelium to touch and interact with said collagen-hydrogel for promoting epithelial cell growth and to respond to said cell growth promoting constituent in the collagen-hydrogel for promoting epithelial cell growth over a healing period where epithelial cells grow over and adhere to said artificial lens implanting the same in the cornea under a new growth layer of corneal epithelium.

Another advantage of the present invention is that the artificial lens formed of a collagen-hydrogel for promoting epithelial cell growth can be implanted by using surgical procedures similar to those used in corneal overlays and corneal inlays which are easier to perform than the implantation of a lens within the corneal stroma as taught by the Swinger/Barraquer Publication.

Another advantage of the present invention is that the step of suturing the artificial lens to Bowman's membrane can be accomplished using suturing techniques presently in the art which include removable suturing material, such as nylon, mersilene, or prolene, or removable devices, such as staples, or biodegradable suturing material, such as pos, vicrylor dexon, by use of the suturing techniques disclosed in U.S. Pat. No. 4,126,904 cited above, suturing through openings formed in the lens, by suturing around the edge thereof by use of a running stitch suturing method known as the "running shoe lace" stitch, suturing by use of individual or "interrupted" sutures, or by use of a biodegradable adhesive which is applied to the posterior surface of an artificial lens formed of the collagen-hydrogel for promoting epithelial cell growth disclosed herein. Also, the artificial lens could be held in place with presently available "therapeutic" contact lenses.

BRIEF DESCRIPTION OF THE DRAWINGS

These and other advantages of this invention will be readily apparent when considered in light of the detailed description hereinafter of the preferred embodiment and when considered in light of the drawing set forth herein which includes the following figures.

DESCRIPTION OF THE PREFERRED EMBODIMENT

Figure 1:
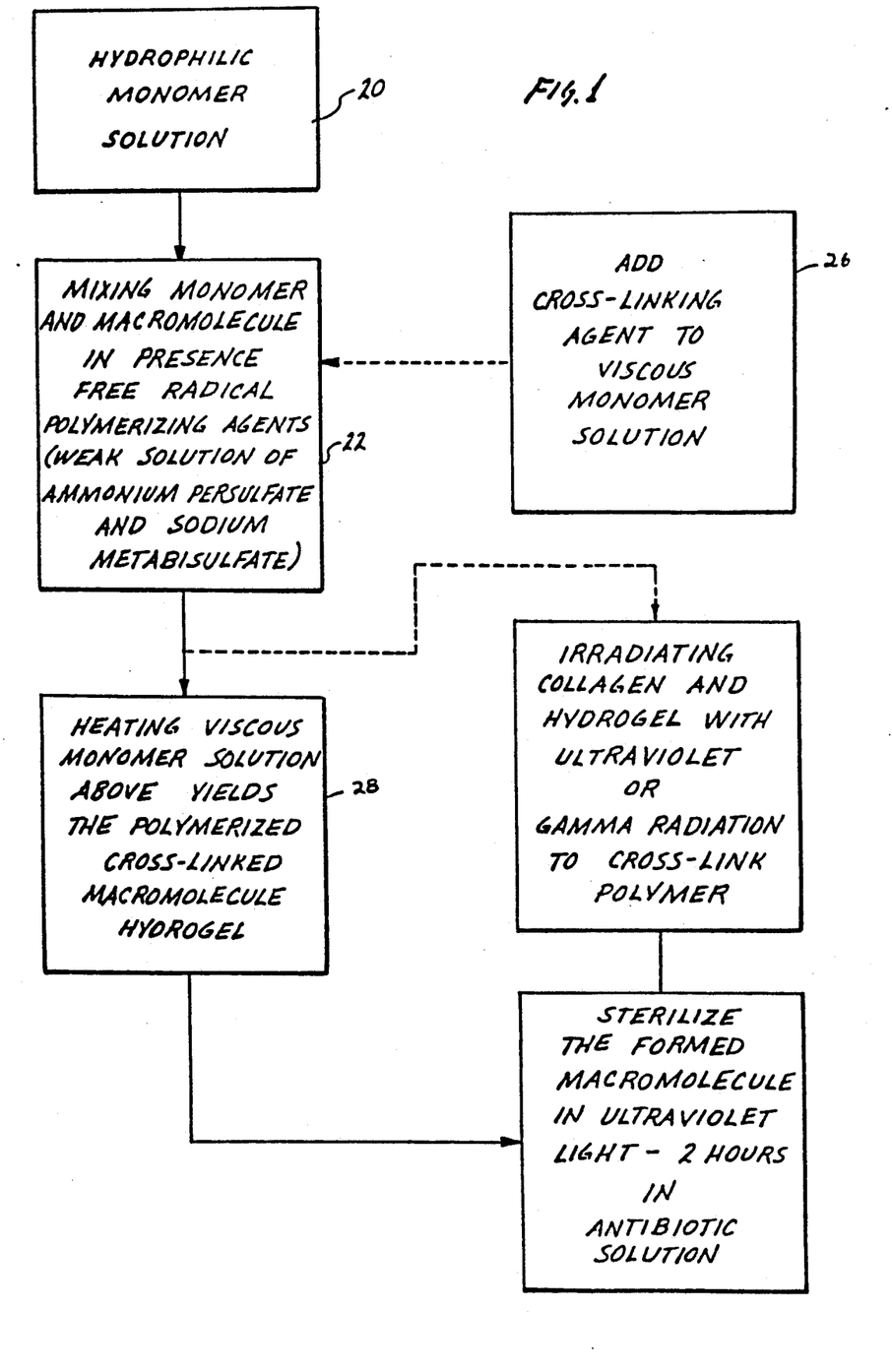
FIG. 1 is a block diagram of the method for producing the collagen-hydrogel for promoting epithelial cell growth of the present invention.

The block diagram of FIG. 1 illustrates the various steps of the preferred method of fabricating a collagen-hydrogel for promoting epithelial cell growth when positioned contiguous to Bowman's membrane and corneal epithelium of the cornea of an eye. The method comprises the step of forming a free radical polymerization of a hydrophilic monomer which is illustrated by block 20 of FIG. 1. The so formed hydrophilic monomer solution used in the step of mixing with an aqueous solution of macromolecules comprising a constituent of ground substance of tissue in the presence of a weak solution of ammonium persulfate and sodium metabisulfate forming a clear viscous monomer solution as illustrated by box 22 of FIG. 1. If the crosslinking agent is to be used to crosslink the polymer during this step, the crosslinking agent is added during the mixing step to insure that the viscous monomer solution had a crosslinking agent therein such that the step of heating will cause the crosslinking to occur to form the polymerized meshwork. The addition of the crosslinking agent to the monomer solution is illustrated by block 26 of FIG. 1.

The next step of heating the viscous monomer solution is illustrated by block 28 of FIG. 1. The heating occurs in the presence of a crosslinking agent to polymerize the same into a three dimensional polymeric meshwork having macromolecules, which are constituent of ground substance of tissue interspersed within the three dimensional polymeric meshwork. If the crosslinking agent was added to the monomer solution during the mixing step as illustrated by blocks 22 and 26, then the crosslinking and interspersing of the macromolecules with the polymeric structure occurs during the heating. By controlling the temperature and heating time of the heating step, the macromolecules are substantially uniformally interspersed with the three dimensional polymeric meshwork.

Alternatively, the crosslinking can be obtained without the heating step, and without the crosslinking agent being in the viscous monomer solution, as is discussed hereinbelow.

If a crosslinking agent is not added to the monomer solution during the mixing phase as described above, the crosslinking can be performed by irradiating the monomer solution during the heating phase with gamma or ultraviolet irradiation. The gamma or ultraviolet irradiation causes the polymerized solution to crosslink and form a three dimensional polymeric meshwork wherein the spaces between the crosslinked molecules of the polymerized hydrophilic monomer contain the macromolecules interspersed therein.

The collagen-hydrogel of this invention differs from those known in the prior art because of the crosslinking of the hydrogel into a three dimension meshwork for anchoring macromolecules capable of supporting anchor-dependent cell growth. Generally hydrogels per se are formed by forming a crosslinked polymer in an aqueous solution to gel the solution. This can be done by free radical polymerization of hydrophilic monomers, such as hydroxyethylmethacrylate (HEMA). This process is well known in the art and is described in Refojo, M. J. (1956), *Journal Applied Polymer Science*, 9, pages 3416-3426, and Holly, H. and Refojo, M. J. (1975), *Journal of Biomedical Material Res.*, 9, page 315. Many other hydrophilic monomers in addition to HEMA can be employed.

As noted hereinabove, the preferred macromolecule added to support cell growth is native collagen, a known substrate for good cell growth. Soluble collagen can be prepared by art-recognized techniques. In addition, other proteins are satisfactory as long as they will support cell attachment and growth. One example of an additional protein known to support cell growth is fibronectin.

Macromolecules in addition to proteins can also be added to these hydrogels as long as they are capable of supporting growth of epithelial cells. Polysaccharides and mucopolysaccharides are one class of such macromolecules, and those skilled in the art will know others.

Small molecules are not employed because they can diffuse throughout the three dimensional meshwork of the crosslinked hydrogel. Since one of the requirements is that the cell growth supporting molecules must be anchored in the meshwork of the hydrogel, only macromolecules are used for promoting growth of epithelial cells. The suitable macromolecules can be water soluble or insoluble, with the former being preferred.

Hydrogel polymers formed by free radical polymerization of monomer solutions, which is the case for HEMA hydrogel, require crosslinking to form the three dimensional polymeric structure of meshwork to gel the aqueous solution HEMA monomer solutions normally contain some dimethacrylate which can crosslink the gel structure. The addition of crosslinking agents such as ethylene glycol dimethacrylate to the polymerization process can change the resultant hydrogel. Generally, the addition of crosslinking agents tend to increase the rigidity and mechanical strength of the hydrogel. Addition of crosslinking agents, such as ethylene glycol dimethacrylate and methymethacrylate, to the polymerization mixture in the presence of native collagen, still changes the physical properties of the hydrogel, and such additions to the polymerization mixture are compatible with the native collagen, and result in the collagen-hydrogel which support growth of epithelial cells. Other known crosslinking agents that can be used satisfactorily in producing the collagen-hydrogel include diacrylates and dimethacrylates or other divalent molecules.

The following examples are of methods for producing the collagen-hydrogel for promoting growth of epithelial cells of the present invention.

EXAMPLE I

Polymers of hydroxyethyl methacrylate (HEMA) are prepared by the method of Refojo, described hereinbefore.

Pepsin soluble collagen is prepared by stirring the ground shaved skin from a one week old calf in 0.5 M acetic acid at 4° C. The residue, after centrifugation, is resuspended in 0.5 M acetic acid containing porcine pepsin at a final enzyme-tissue ratio of 1:50 (wet weight) and allowed to stir overnight. The stabilized, collagen is then precipitated by addition of solid NaCl to a concentration of 5%. The resulting precipitate is resolubilized in 0.5 M acetic acid, then dialyzed exhaustively versus 0.02 M $Na_2HPO_4$, pH 7.44 at 4° C. Following dialysis, the precipitate is subjected to differential NaCl precipitation at pH 7.44 as described in Chung, E. and Miller, E. J. (1974), *Science*, 183, pages 1200-1201. These precipitates are then lyophilized and suspended in 0.5 M acetic acid at a concentration of 1.2-1.4 mg/ml as determined by hydroxyproline content, and allowed to stir overnight at 4° C. The resulting solution is dialyzed against 0.15 M NaCl—0.05 M Tris, pH 7.44, overnight at 4° C. This solution is used as a stock solution of collagen.

One ml of commercial HEMA, 1.0 ml of ethylene glycol, 1.0 ml of $H_2O$ or buffer or stock solution of collagen (properly diluted). 0.1 ml of 6% ammonium persulfate and 0.1 ml of 12% sodium metabisulfate are added in sequence. A (quantity 0.1 ml of ethylene glycol dimethacrylate), a crosslinking agent, is added to the solution. After mixing, the resulting clear viscous monomer solution is heated for two hours at 38° C., in a mold, as used in the production of a contact lens. The resulting clear flexible collagen-hydrogel is then dialyzed exhaustively versus the Tris-NaCl buffer, pH 7.44, to remove residual monomer and ethylene glycol. During dialysis, the collagen-hydrogel membranes become opaque, but transparency returns once the ethylene glycol has been exchanged for water.

EXAMPLE II

A collagen-hydrogel monomer viscous solution is prepared as in EXAMPLE I except that the ammonium persulfate and sodium metabisulfate are not added to the solution. The collagen-hydrogel is exposed to gamma radiation or ultra violet radiation for two hours to polymerize the monomer solution. The resulting collagen-hydrogel, is sterilized in Puck's $Ca^{++}Mg^{++}$ free saline containing 1,000 units penicillin, 50 ml Aureomycin, and 0.25 ml Fungizoine per ml of medium and placed under an ultraviolet light for two hours. The collagen-hydrogel is then transferred to a Puck's saline containing penicillin and streptomycin and stored at 4° C. prior to use.

(End of examples)

Collagen-hydrogel which contain HEMA alone, or HEMA, ethylene glycol dimethacrylate and methymethacrylate, and all combinations thereof, in strata, support various other cell growth lines in tissue culture. Specifically, the so formed collagen-hydrogels successfully supported growth of the following cell lines:
(1) Rabbit smooth muscle cells;
(2) Calf smooth muscle cell;
(3) Lung endothelial cells; and
(4) Lung epithelial cell.

It is likely that the collagen-hydrogel disclosed herein can serve as strata for growth of all cells of all classes, epithelial, endothelial and mesothelial, which appear to be compatible with cells of all tissues, including corneal epithelial cells.

Figure 2:
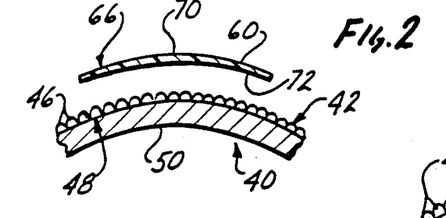
FIG. 2 is a pictorial representation of an eye showing the relationship between corneal epithelium, Bowman's membrane and the corneal stroma and a representation of an artificial lens formed of the collagen-hydrogel for promoting epithelial cell growth which is adapted to be implanted with the eye using the surgical procedures set forth herein.

FIG. 2 illustrates pictorially the method of positioning an artificial lens, fabricated from the collagen-hydrogel as described above, and formed of a predetermined geometrical shape and lenticular power, such as a contact lens, to the cornea. The eye, shown generally as 40, has a corneal epithelium 42 formed of layers of epithelial cells illustrated graphically as humps 46. Below corneal epithelium 42 is Bowman's membrane 48, which supports corneal epithelium. Below Bowman's membrane is the corneal stroma 50. An artificial lens, such as for example a contact lens having an optical portion, 60 is positioned above corneal epithelium to illustrate the size thereof.

Figure 3:
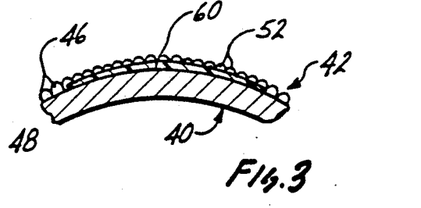
FIG. 3 is a pictorial representation of an eye showing the relationship between an implanted artificial lens shown in FIG. 2 implanted between Bowman's membrane and corneal epithelium after the eye has healed and the epithelial cells have grown to several layers in thickness and form corneal epithelium which is attached to and covers the anterior surface of the artificial lens.

FIG. 3 illustrates pictorially the preferred location of the contact lens 60 in the eye after the healing process. The contact lens 60 is located between Bowman's membrane and corneal epithelium after new epithelial cells 52 have grown during the healing process to cover the anterior surface of the lens 60.

Figure 4:
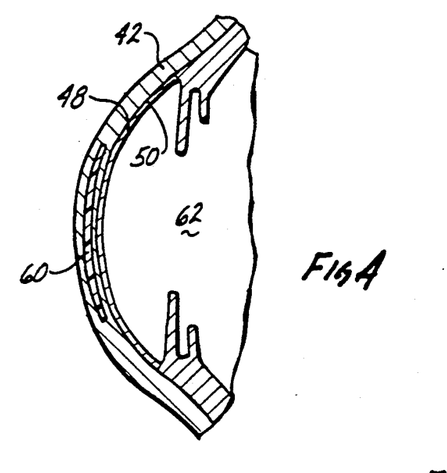
FIG. 4 is a cross sectional view of an eye illustrating that the implanted artificial lens illustrated pictorially in FIG. 2 overlies the pupillary zone of the eye and that the same is in the form of a corneal inlay after the healing process.

FIG. 4 illustrate that the contact lens is positioned over the pupillary zone 62 of the eye and implanted between Bowman's membrane 48 and corneal epithelium 42.

FIGS. 5 through 10 disclose a method for locating on the cornea an optical lens, which may be an artificial lens such as a contact lens, having a preselected geometric shape and lenticular power wherein the optical lens comprises an optical portion having an outer edge 66, an anterior surface 70 and a posterior surface 72, the elements 66, 70 and 72 being shown in FIG. 2. For purposes of the steps illustrated in FIGS. 5 through 10, the artificial lens has been fabricated from the collagen-hydrogel, and the specific contact lens has been formed by (i) a contact lens mold, or (ii) frozen collagen-hydrogel which has been lathed, so as to form a contact lens of a predetermined shape and power. Prior to placement of the lens on the cornea, the contact lens is sterilized by exposure to ultraviolet light.

Figure 5:
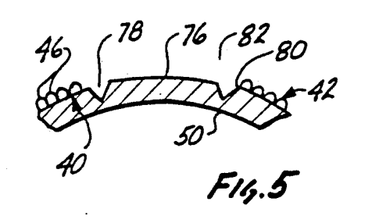
FIG. 5 illustrates pictorially the first steps of the surgical procedure of removing a portion of corneal epithelium to expose a portion of Bowman's membrane and forming an annular shaped "V" groove wherein the "V" shaped groove has a peripheral edge and medial edge.

FIG. 5 illustrates the first step of the surgical method, that step being the removing from Bowman's membrane 40, over the pupillary zone of the eye, a portion of corneal epithelium on an area slightly greater than the generalized shape of said optical lens, which area is represented by area 76. This step is similar to the removal of corneal epithelium from the anterior surface of the cornea in the Epikeratophakia Procedure.

Thereafter, the next step is that of forming on Bowman's membrane 40 a "V" shaped annular groove 78 having a diameter substantially equal to the maximum geometrical dimensions of the optical lens 60 and defining therearound a peripheral edge 80 and a medial edge 82. The "V" shaped, annular groove 78 has a preselected depth which is less than the thickness of the corneal stroma 50. Typically, the groove is formed to have a depth of about 0.3 mm, and the depth is prepared in the cornea utilizing a 7 mm trephine.

Figure 6:
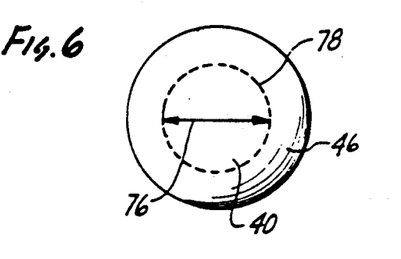
FIG. 6 illustrates pictorially that the area of removed corneal epithelium is generally circular in shape and that the "V" shaped groove is located peripherally within the area of removed corneal epithelium.

FIG. 6 illustrates, by means of a front view, the cornea showing the area 76 of corneal epithelium 46 that has been removed from and to expose the area of Bowman's membrane 40 from which corneal epithelium 46 has been removed. Also, the annular shape of the "V" groove 78 is illustrated.

Figure 7:
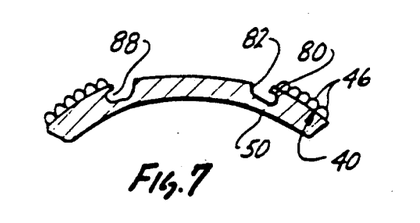
FIG. 7 illustrates pictorially the corneal wing that is formed in the peripheral edge of the annular "V" shaped groove.

FIG. 7 shows the next step of dissecting the peripheral edge 80 of the groove 78 forming a wing 88 of corneal tissue having a preselected length. This step is performed by the surgeon in the following manner. As in an Epikeratophakia Procedure, a cornealspreading instrument is used to dissect the peripheral edge 80 of the groove 78 forming a corneal wing, preferably of about 1.5 mm in length. The edge 66 of the optical lens 60 is to be located under the corneal wing 88. The medial edge 82 is cut free of the globe, i.e. the curved surface of Bowman's membrane 40.

Figure 8:
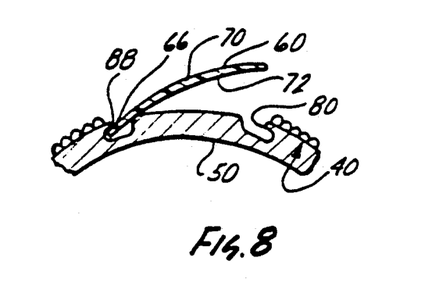
FIG. 8 illustrates the insertion of the edge of the artificial lens under the corneal wing.

FIG. 8 illustrates the next step of placing the posterior surface 72 of the optical lens 60 on the anterior surface of Bowman's membrane and positioning the outer edge 66 of the optical lens 60 under the corneal wing 88.

Figure 9:
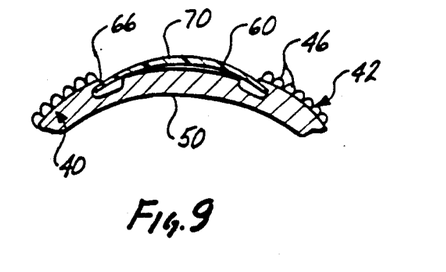
FIG. 9 illustrates pictorially the relationship of the edge of the artificial lens under the corneal wing after completion of the surgery and before the healing process.
Figures 10, 11, 12, 13, 14, 15, 16, 17, 18:
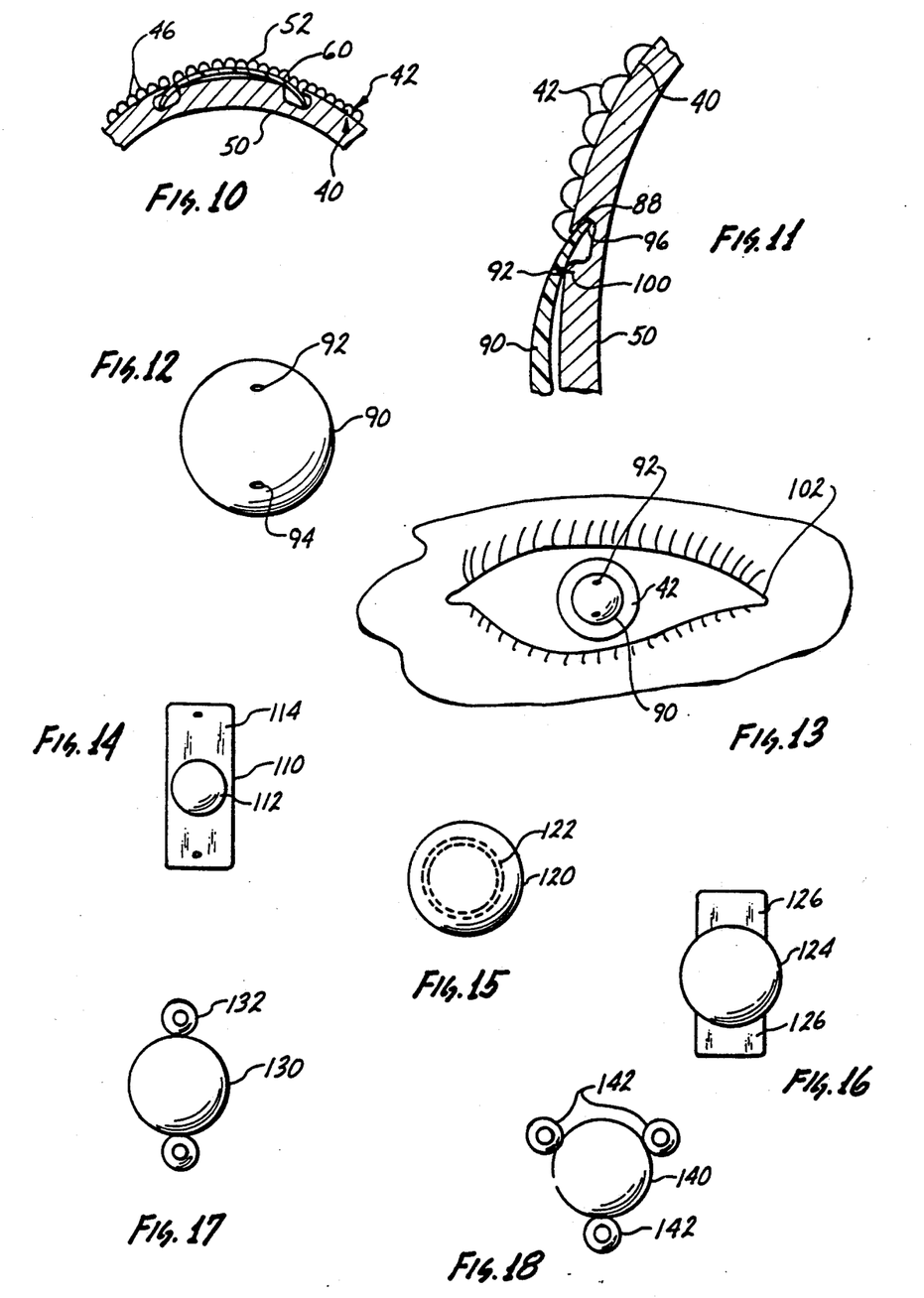
FIG. 10 illustrates pictorially the relationship of the edge of the artificial lens under the corneal wing after completion of the surgery and after the healing process wherein the epithelial cells have grown to form corneal epithelium implanting the lens between Bowman's membrane and corneal epithelium.
FIG. 11 is a partial cross section showing the use of a removable suturing material for affixing the artificial lens to the cornea after the lens has been positioned in place as illustrated in FIG. 10.
FIG. 12 is a representation of a circular shaped lens having two openings formed therein to permit the means for performing the suturing step illustrated in FIG. 11.
FIG. 13 is a pictorial representation of a complete eye illustrating the sutured lens on the cornea.
FIG. 14 is a representation of a rectangular shaped artificial lens having an optical portion and edges which can be used to suture the lens in position over the pupillary zone of the eye.
FIG. 15 is a representation of a circular shaped artificial lens formed of the collagen-hydrogel for promoting epithelial cell growth of this invention and having an implanted ring of material having different optical properties than that of the collagen-hydrogel for promoting epithelial cell growth and which provides differential passage of an image to the retina and which is of a, size and shape to be implanted on the cornea using the teachings of this invention.
FIG. 16 is a representation of a circular shaped artificial lens formed from the collagen-hydrogel for promoting epithelial cell growth disclosed herein having tabs extending therefrom which may be used by a surgeon in implanting the artificial lens in the eye using the teachings of this invention.
FIG. 17 is a representation of a circular shaped artificial lens formed from the collagen-hydrogel for promoting epithelial cell growth disclosed herein having two aligned circular support members extending opposite direction therefrom which may be used by a surgeon in implanting the artificial lens in the eye using the teachings of this invention.
FIG. 18 is a representation of a circular shaped artificial lens formed from the collagen-hydrogel for promoting epithelial cell growth disclosed herein having three circular tabs spaced equidistantly around the periphery of an optical lens which may be used by a surgeon in implanting the artificial lens in the eye using the teachings of this invention.

FIG. 9 illustrates the final position of the lens 60 over the pupillary zone of the eye before the optical lens is attached to or affixed to the eye. The attachment can be performed in any number of procedures, one of which is illustrated in FIG. 11. FIG. 9 is then a representation of the optical lens in the eye at the end of the surgical procedure, and before the healing process. It is pointed out that the anterior surface of the lens 60 is free of any cell growth. As illustrated in FIG. 9, the edge 66 of the lens 60 is positioned relative to and in contact with corneal epithelium 42 and the corneal wing 88 (shown in FIGS. 7 and 11) lies flush with the anterior surface of the optical lens 60.

FIG. 10 is a representation of the condition of the eye at the end of the healing process.

As shown in FIG. 10, the edge 66 of the lens 60 is positioned so as to enable the epithelial cells to touch and interact with the collagen-hydrogel lens 60 to promote epithelial cell growth over a healing period. During the healing period, new epithelial cells 52 grow over and adhere to the anterior surface 70 of the optical lens 60, implanting the same in the cornea under a new growth of corneal epithelium 42 formed from several layers of new epithelial cells.

FIG. 11 illustrates one method of suturing a lens to Bowman's membrane wherein the optical lens includes at least two openings therein adjacent the outer edge thereof. Such a lens is illustrated in FIG. 12 as lens 90 having openings 92 and 94. As illustrated in FIG. 11, the lens 90 is affixed to Bowman's membrane by the step of suturing the optical lens 90 to Bowman's membrane through the openings 92 and 94. The suture material is shown as a single loop stitch 100 in FIG. 11.

In the alternative, the lens 60, illustrated in FIGS. 9 and 10, could be affixed to Bowman's membrane by the step of bonding with a biodegradable adhesive the posterior surface 72 of the optical lens to Bowman's membrane 40.

The method of affixing the lens to Bowman's membrane can be accomplished with either a removable or biodegradable suturing material, staples or the like. One preferred method for insuring that the lens 90 does not separate from Bowman's surface resulting in the edge 96 moving from under the corneal wing 88 is to utilize the step of suturing the optical lens 90 to Bowman's membrane with a biodegradable suturing material in the form of a running "shoe lace" stitching which passes through the outer edge of the optical lens 90 and Bowman's membrane 40.

FIG. 13 illustrates in a front view, after completion of locating the lens on the cornea of the eye and before beginning the healing process, the relationship of the eye 90 to the cornea wherein the lens 90, of FIGS. 11 and 12, is sutured to Bowman's membrane through openings 92 and 94 of the lens 90.

FIG. 14 illustrates a possible lens configuration for an artificial lens 110 having an optical portion 112 configured for placement over the pupillary zone of the eye and on the central anterior surface of Bowman's membrane of the cornea having corneal epithelium thereof removed. The optical portion terminates in end tabs 114 and is formed such that the optical portion is dimensioned to substantially cover the total anterior surface of the pupillary zone of an eye. The entire lens 110 including the optical portion 112 and tabs 114 is formed of a collagen-hydrogel for promoting epithelial cell growth.

FIG. 15 is a representation of a circular shaped artificial lens 120 formed of the collagen-hydrogel for promoting epithelial cell growth and having implanted therein a ring 122 of material having different optical properties than that of the collagen-hydrogel for promoting epithelial cell growth used in the lens 120. The ring 122 functions to focus at the center thereof while the outer edge of the ring 122 passes light to the retina. This results in a differential passage of an image to the retina. The lens 120 is of a size and shape to be implanted on the cornea using the teachings of this invention.

FIG. 16 is a representation of a circular shaped optical portion 124 of an artificial lens formed from the collagen-hydrogel for promoting epithelial cell growth disclosed herein having tabs 126 extending therefrom which may be used by a surgeon in implanting the artificial lens in the eye using the teachings of this invention. The optical portion 124 and the tabs 126 are formed of the collagen-hydrogel.

FIG. 17 is a representation of a circular shaped artificial lens having an optical portion 130 formed from the collagen-hydrogel for promoting epithelial cell growth disclosed herein and two aligned circular support members 132 extending in opposite directions from the optical portion 130 which may be used by a surgeon in implanting the artificial lens in the eye using the teachings of this invention. The optical portion 130 and the tabs 132 are formed of the collagen-hydrogel.

FIG. 18 is a representation of a circular shaped artificial lens formed from the collagen-hydrogel for promoting epithelial cell growth disclosed herein wherein the optical portion 140 has three circular tabs or support members 142 having apertures formed therein spaced equidistantly around the periphery of an optical lens portion 140. The support members 142 may be used by a surgeon in implanting the artificial lens in the eye using the teachings of this invention. The optical portion 130 and the tabs 132 are formed of the collagen-hydrogel.

It is envisioned that the collagen-hydrogel of the present invention, and artificial lens formed from the collagen-hydrogel, can be used for epicorneal, corneal or transcorneal lenses which are capable of promoting and supporting epithelial cell growth during the healing period. During the healing process, a bandage contact lens may be placed on the eye until the anterior surface of the lens is covered by corneal epithelium.

The collagen-hydrogel biomedical material disclosed herein has, in its preferred embodiment, application in the artificial lens field because of the properties of the collagen-hydrogel promoting the growth of epithelial cells. It is envisioned that such collagen-hydrogel could be used as substrata for support of growth of other cells in the human body wherein the hydrogel could be formed of any one of a number of monomers of the hydrophilic class of polymers, and that other so formed hydrogels when used in a collagen-hydrogel with appropriate macromolecules as described herein could be used to enable the growth of other classes of human tissue other than epithelial cells.

What is claimed is:

1. The method of producing a collagen-hydrogel for promoting epithelial cell growth when positioned contiguous to the Bowman's membrane and corneal epithelium of the cornea of an eye comprising the steps of
    forming a radical free polymer of a hydrophilic monomer;
    mixing the hydrophilic monomer with a diluted solution of macromolecules comprising a constituent of ground substance of tissue in the presence of a weak solution of ammonium persulfate and sodium metabisulfate forming a clear viscous monomer solution;
    heating said viscous monomer solution in a mold in the presence of a crosslinking agent to polymerize the same into a three dimensional polymeric meshwork having macromolecules comprising a constituent of ground substance of tissue interdispersed within the three dimensional polymeric meshwork.

2. The method of producing a collagen-hydrogel of claim 1 wherein during the step of heating, said macromolecules comprising a constituent of ground substance of tissue are heated a sufficient period of time at a selected temperature to enable the macromolecules to substantially uniformly interdisperse within the three dimensional polymeric meshwork.

3. The method of producing a collagen-hydrogel of claim 1 wherein during the step of heating the following step is performed:
    irradiating the heated viscous monomer solution with ultraviolet radiation, as the crosslinking agent, to polymerize said viscous monomer solution to form said three dimensional polymeric meshwork.

4. The method of producing a collagen-hydrogel lens for promoting epithelial cell growth when positioned contiguous to Bowman's membrane and corneal epithelium of the cornea of an eye comprising the steps of
    forming a radical free polymer of a hydrophilic monomer;
    mixing the hydrophilic monomer with a diluted solution of macromolecules comprising a constituent of ground substance of tissue in the presence of a weak solution of ammonium persulfate and sodium metabisulfate forming a clear viscous monomer solution;
    heating said viscous monomer solution in a lens mold having a predetermined shape to form a lens of a selected power in the presence of a crosslinking agent to polymerize the same into a three dimensional polymeric meshwork having macromolecules comprising a constituent of ground substance of tissue interdispersed within the three dimensional polymeric meshwork and forming an artificial lens of a predetermined shape and power.

5. The method of producing a collagen-hydrogel lens of claim 4 further comprising the step of
sterilizing the lens formed of the collagen-hydrogel material.

6. The method of producing a collagen-hydrogel lens of claim 4 further comprising the step of
sterilizing the lens formed of the collagen-hydrogel material with an ultraviolet source of actinic radiation.

7. The method of producing a collagen-hydrogel lens for promoting epithelial cell growth when positioned contiguous to Bowman's membrane and corneal epithelium of the cornea of an eye comprising the steps of
forming a radical free polymer of a hydrophilic monomer;
mixing the hydrophilic monomer with a diluted solution of macromolecules comprising a constituent of ground substance of tissue in the presence of a weak solution of ammonium persulfate and sodium metabisulfate forming a clear viscous monomer solution;
heating said viscous monomer solution in the presence of a crosslinking agent to polymerize the same into a three dimensional polymeric meshwork having macromolecules comprising a constituent of ground substance of tissue interdispersed within the three dimensional polymeric meshwork; and
freezing the crosslinked and polymerized hydrogel-collagen material in a lens mold having a predetermined shape to form a lens of a selected power to form an artificial lens of a predetermined shape and power.

8. A method of producing a collagen-hydrogel comprising the steps of
forming a radical free polymer of a hydrophilic monomer;
mixing the hydrophilic monomer with a stock solution of collagen in the presence of a weak solution of ammonium persulfate and sodium metabisulfate forming a clear viscous monomer solution; and
heating said viscous monomer solution in the presence of a crosslinking agent to polymerize the same into a three dimensional polymeric meshwork having collagen from the stock solution of collagen interdispersed within the three dimensional polymeric meshwork.

9. The method of producing a collagen-hydrogel of claim 8 wherein heating is for a sufficient period of time at a selected temperature to enable the collagen to substantially uniformly interdisperse within the three dimensional polymeric meshwork.

10. The method of producing a collagen-hydrogel of claim 8 wherein during the step of mixing a cross-linking agent is added to the viscous monomer solution.

11. The method of producing a collagen-hydrogel of claim 8 wherein during the step of heating the following step is performed:
irradiating the heated viscous monomer solution with ultraviolet radiation, as the crosslinking agent, to polymerize said viscous monomer solution to form said three dimensional polymeric meshwork.

12. The method of producing a collagen-hydrogel lens for promoting epithelial cell growth when positioned contiguous to Bowman's membrane and corneal epithelium of the cornea of an eye comprising the steps of
forming a radical free polymer of a hydrophilic monomer;
mixing the hydrophilic monomer with a stock solution of collagen comprising a constituent of a ground substance of tissue in the presence of a week solution of ammonium persulfate and sodium metabisulfate forming a clear viscous monomer solution; and
heating said viscous monomer solution in a mold having a predetermined shape to form a lens of a selected power in the presence of a crosslinking agent to polymerize the same into a three dimensional polymeric meshwork having collagen from the stock solution of collagen interdispersed within the three dimensional polymeric meshwork and forming an artificial lens of a predetermined shape and power.

13. The method of producing a collagen-hydrogel lens of claim 12 further comprising the step of
sterilizing the lens formed of the collagen-hydrogel material.

14. The method of producing a collagen-hydrogel lens of claim 12 further comprising the step of
sterilizing the lens formed of the collagen-hydrogel material with an ultraviolet source of actinic radiation.

15. The method of producing a collagen-hydrogel lens for promoting epithelial cell growth when positioned contiguous to Bowman's membrane and corneal epithelium of the corneal of an eye comprising the steps of
forming a radical free polymer of a hydrophilic monomer;
mixing the hydrophilic monomer with a stock solution of collagen comprising a constituent of a ground substance of tissue in the presence of a weak solution of ammonium persulfate and sodium metabisulfate forming a clear viscous monomer solution;
heating said viscous monomer solution in the presence of a crosslinking agent to polymerize the same into a three dimensional polymeric meshwork having collagen from the stock solution or collagen interdispersed within the three dimensional polymeric meshwork; and
freezing the crosslinked and polymerized hydrogel-collagen material in a mold having a predetermined shape to form a artificial lens of a predetermined shape and power.

16. A method of producing a collagen-hydrogel for promoting cell growth comprising the steps of
forming a radical free polymer of a hydrophilic monomer;
mixing the hydrophilic monomer with a stock solution of collagen forming a clear viscous monomer solution; and
heating said viscous monomer solution in the presence of a crosslinking agent to polymerize the same into a three dimensional polymeric meshwork having collagen from the stock solution of collagen interdispersed within the three dimensional polymeric meshwork.

17. The method of producing a collagen-hydrogel of claim 16 wherein the step of mixing includes using a stock solution of collagen comprising a ground substance of tissue.

18. The method of producing a collagen-hydrogel of claim 16 wherein during the step of mixing a cross-linking agent is added to the viscous monomer solution.

19. The method of producing a collagen-hydrogel of claim 18 wherein the heating is for a sufficient period of time at a selected temperature to enable the collagen to substantially uniformly interdisperse within the three dimensional polymeric meshwork.

20. The method of producing a collagen-hydrogel of claim 16 wherein during the step of heating the following step is performed:

irradiating the heated viscous monomer solution with ultraviolet radiation, as the crosslinking agent, to polymerize said viscous monomer solution to form said three dimensional polymeric meshwork.

21. The method of producing a collagen-hydrogel of claim 16 wherein the step of forming a radical free polymer hydrophilic monomer includes the step of forming a radical free polymer of hydroxyethylmethacrylate.

22. The method of producing a collagen-hydrogel of claim 16 wherein said heating of said viscous monomer solution is in the presence of ethylene glycol dimethacrylate.

23. The method of producing a collagen-hydrogel of claim 16 wherein said heating of said viscous monomer is in the presence of methymethacrylate.

24. The method of producing a collagen-hydrogel of claim 17 further comprising the step of harvesting native collagen as the ground substance of tissue from tissues of human cornea, livestock cornea of calf's or livestock's skins.

25. The method of producing a collagen-hydrogel of claim 17 further comprising the step of deriving native collagen as the ground substance of tissue from animal sources which are capable of promoting and supporting growth of epithelial cells.

26. The method of producing a collagen-hydrogel of claim 17 wherein further comprising the step of deriving native collagen as the ground substance of tissue from mucopolysaccharia which is capable of promoting and supporting growth of epithelial cells.

27. The method of producing a collagen-hydrogel of claim 17 wherein further comprising the step of deriving native collagen as the ground substance of tissue from fibronectin which is capable of promoting and supporting growth of epithelial cells.

* * * * *